United States Patent [19]

Harada et al.

[11] Patent Number: 5,382,610
[45] Date of Patent: Jan. 17, 1995

[54] WATER ABSORBENT MATTER AND METHOD FOR PRODUCING IT AS WELL AS WATER ABSORBENT AND METHOD FOR PRODUCING IT

[75] Inventors: Nobuyuki Harada; Katsuyuki Wada; Hisanori Obara; Tadao Shimomura, all of Osaka; Yoshinori Sano, Hyogo, all of Japan

[73] Assignee: Nippon Shokubai Co., Ltd., Osaka, Japan

[21] Appl. No.: 144,104

[22] Filed: Oct. 27, 1993

Related U.S. Application Data

[63] Continuation of Ser. No. 810,083, Dec. 19, 1991, abandoned.

[30] Foreign Application Priority Data

Dec. 21, 1990 [JP] Japan .................. 2-404911
Aug. 1, 1991 [JP] Japan .................. 3-193278
Aug. 1, 1991 [JP] Japan .................. 3-193279

[51] Int. Cl.6 .................. C08L 1/00; A61F 13/15; A61F 13/20
[52] U.S. Cl. .................. 524/35; 524/13; 428/221; 604/358; 604/367; 604/372; 525/183; 525/187
[58] Field of Search .................. 524/13, 35, 36, 39; 428/507, 233, 243; 604/358, 367, 372; 525/183, 187

[56] References Cited

U.S. PATENT DOCUMENTS

| 3,888,257 | 6/1975 | Cook et al. .................. 128/296 |
| 4,058,124 | 11/1977 | Yen et al. .................. 524/13 |
| 4,242,242 | 12/1980 | Allen .................. 524/35 |
| 4,647,617 | 3/1987 | Saotome .................. 524/13 |
| 4,666,983 | 5/1987 | Tsubakimoto et al. .................. 525/119 |

FOREIGN PATENT DOCUMENTS

| 57-34101 | 2/1982 | Japan . |
| 57-44627 | 3/1982 | Japan . |
| 58-35605 | 8/1983 | Japan . |
| 60-36516 | 2/1985 | Japan . |
| 60-163956 | 8/1985 | Japan . |
| 60-255814 | 12/1985 | Japan . |
| 62-54751 | 3/1987 | Japan . |
| 62-16135 | 4/1987 | Japan . |
| 62-144748 | 6/1987 | Japan . |
| 62-21902 | 1/1988 | Japan . |
| 63-19215 | 4/1988 | Japan . |
| 1-17411 | 3/1989 | Japan . |
| 2-14361 | 4/1990 | Japan . |
| 2-248404 | 10/1990 | Japan . |

*Primary Examiner*—Veronica P. Hoke
*Assistant Examiner*—LaVonda R. DeWitt
*Attorney, Agent, or Firm*—Armstrong, Westerman, Hattori, McLeland & Naughton

[57] ABSTRACT

The present invention provides a water absorbent matter which is physically and chemically stable, difficult in shifting and falling-off of a water-absorbent resin particle and from a cellulose fiber, and thereby, has superior water-absorbent properties. A water absorbent matter like this is made by containing a water-absorbent resin particle having an acidic group such as a carboxyl group on the surface, a cellulose fiber, and a cationic high-molecular compound having a weight-average molecular weight of 2,000 or more, so that the water-absorbent resin particle is firmly set on the cellulose fiber by a cationic high-molecular compound in the presence of water.

29 Claims, 1 Drawing Sheet

WATER ABSORBENT MATTER AND METHOD FOR PRODUCING IT AS WELL AS WATER ABSORBENT AND METHOD FOR PRODUCING IT

This application is a continuation of application Ser. No. 810,983 filed Dec. 19, 1991 now abandoned.

BACKGROUND OF THE INVENTION

The present invention relates to a new water absorbent matter and a method for producing this matter. In detail, this invention relates to a new water absorbent matter, which is consisting of a mixture of a cellulose fiber and a water-absorbent resin particle and which is stable physically and chemically even after absorbing a liquid, and it relates to a method for producing this matter.

The present invention relates to a method for producing a new type water absorbent. In detail, the invention relates to a method for producing a water absorbent which shows superior water-absorbent properties by a sole use of the water absorbent and displays a very superior water-absorbent effect in a case of being converted into a complex with a cellulose fiber.

The present invention relates to a new water absorbent, an absorbent matter containing this absorbent, and a method for producing these. In detail, the present invention relates to a new water absorbent having a superior water-absorbent property in its sole use and also, displaying a very superior effect in a case where it makes a complex with a cellulose fiber, as well as it relates to an absorbent matter containing the water absorbent and a method for producing this absorbent and matter.

In recent years, water-absorbent resins which are able to absorb water in a range of from several ten times of their own weight to several hundred times have been developed, and, various kinds of the water-absorbent resins have been used for usage which needs water-absorption and water-holding, that is in the fields of sanitary materials such as goods for menstrual periods and disposable diapers, etc., of agriculture and gardening, of foods such as freshness maintenance, etc., and of industries such as materials for preventing dew-forming and for maintaining refrigeration, etc. As the water-absorbent resin there have been already known cross-linked polyacrylates and crosslinked starch-polyacrylate graft polymers.

Since the water-absorbent resin is generally powder, its sole use is few and it is used as a water absorbent matter such as a diaper etc. by mixing it with a hydrophilic fiber such as pulverized pulp, paper, or the like (for example, refer to U.S. Pat. No. 3,888,257 and others). In an use which requires to absorb a lot of water in a short period of time, a sole use of the water-absorbent resin is not enough to absorb the water in a short period of time and, thus, to prevent water-spreading, mixing of the above kind is particularly necessary. The cellulose fiber has a function of holding a powder type water-absorbent resin and, since the water-absorbent resin takes time to absorb water, a function of holding water around water-absorbent resin particles until the time necessary for absorption, and a function of spreading water to the water-absorbent resin particles distributed by a capillary tube phenomenon.

There have so far been offered a quite number of proposals for the method for elevating a water-absorbing velocity and a water absorption amount under pressure. For example, in Japanese Official Patent Gazette, showa 63-19215, there has been disclosed a method which comprises mixing a water-absorbent resin powder having a carboxyl group with a polyvalent amine compound and, if necessary, thermally treating to crosslink a molecular chain adjacent to the surface. In Japanese Official Patent Gazette, heisei 1-17411, there has been disclosed a method which comprises mixing a water-absorbent resin powder having a carboxyl group with a polyvalent alcohol and a compound of one kind or two or more kinds selected from a group consisting of water and a hydrophilic organic solvent in proportions of from about 0.001 to 10 parts by weight of the polyvalent alcohol and from about 0.01 to 8 parts by weight of the compound against 100 parts by weight of the water-absorbent resin powder, heating the mixture at a temperature of more than 90° C. to carry out a reaction of the water-absorbent powder with the polyvalent alcohol, and crosslinking a molecular chain adjacent to a surface of the water-absorbent resin powder. In Japanese Official Patent Provisional Publication, showa 57-44627, there has been disclosed a method which comprises dispersing a water-absorbent resin containing an acrylic acid alkali salt as a component constituting a polymer, adding a crosslinking agent having two or more of a functional group capable of reacting with a carboxyl group (for example, ethyleneglycohol diglycidyl ether), and carrying out the crosslinking. In Japanese Official Patent Provisional Publication, showa 60-163956, there has been disclosed a method which comprises, in the presence of a water-absorbent resin which contains a monomer unit having a carboxylate as a component constituting a polymer and an inert inorganic powder (water-containing silicon dioxide, etc.), absorbing a crosslinking agent (a diglycidyl ether-based compound, a polyvalent metal salt, a haloepoxy-based compound, an aldehyde-based compound, and an isocyanate-based compound, etc.) and water and then, heating with stirring to carry out a crosslinking reaction and water-distillation. In Japanese Official Patent Provisional Publication, showa 60-36516, there has been disclosed a method which comprises immersing followed by polymerizing a hydrophilic monomer having a functional group reactive for a highly water-absorbent resin having a carboxyl group, of which water content is adjusted at 50% by weight or less [a nitrogen-containing vinyl monomer such as (meth)acrylamide and N,N-dimethylaminoethyl methacrylate; a oxygen-containing vinyl monomer such as 2-hydroxyethyl methacrylate; a sulfonate-containing vinyl monomer such as vinyl sulfonate; and a nitrile group-containing vinyl monomer such as acrylonitrile, etc.]. In Japanese Official Patent Provisional Publication, 60-255814, there has been disclosed a method which comprises adding by spraying a crosslinking agent (diglycidyl ether-based compound, a polyvalent metal salt, and a haloepoxy-based compound) under a condition of stirring a water-absorbent resin containing a monomer unit having a carboxylate group as a component constituting a polymer and an inert inorganic powder, then heating to carry out a crosslinking reaction, and then distilling-off water. In Japanese Official Patent Provisional Publication, heisei 2-248404, there has been disclosed a method which comprises crosslinking a water-insoluble, highly water-absorbent resin having a COOM group (M is a hydrogen atom or an alkali metal atom) in a side chain by a reaction product from epihalohydrine and ammonia or an amine. However, the water absorbent matter obtained from the abovementioned arts known in public, for example, in a case where it is used as a water absorbent matter for disposable diapers, because a binding force among cellulose fibers is weaker when a proportion of the water-absorbent resin particles becomes higher, there takes place in an actual use the moving and falling-off of a water-absorbent resin swelled after urine-absorbing and, thereby, there has been found a problem that the water-absorbent performance does not appear as in an expected degree or a problem that the performance does not appear as projected, because the water-absorbent resin particles decomposes by an ingredient in urine.

Also, a water-absorbent resin improved by the above-mentioned arts known in public shows in some degree elevation in the water-absorbent property of the water-absorbent resin itself, but in the case where the resin was mixed to make a complex with a cellulose fiber, the water-absorbent property was unsatisfactory. Especially, when a proportion of the water-absorbent resin becomes higher, a binding force among cellulose fibers becomes weaker, so that there easily occurs the falling-off of the water-absorbent resin. This defect has been known in some examples at the present stage; for example, in a case where the water-absorbent resin is used as a part of a water-absorbent matter in a disposable diaper, the water-absorbent resin swelled after urine-absorption shifts or falls off due to movement of a wearing body, thereby the water-absorbent performance is not displayed in such an extent as expected. Such a phenomenon as the shifting and falling off of the water-absorbent resin is a great handicap in various use of the water-absorbent resin. In practical use, although it may be said that an ideal water-absorbent resin is such as capable of sufficiently deriving an effect mutually potentiating (a synergistic effect) with a complex-making partner material such as a cellulose fiber etc., such one as well as a water absorbent matter not showing the moving and falling-off of a water absorbent resin after absorbing water are not yet obtained at the present stage.

SUMMARY OF THE INVENTION

An object of the present invention is to provide a water absorbent matter which is physically and chemically stable and has a superior water-absorbent property because of the difficulty in shifting and falling-off among the cellulose fibers of water-absorbent resin particles. Further, an object of the present invention is to provide a method for producing such a water absorbent matter as the above.

An object of the present invention is to provide a method for easily producing a water absorbent which does not shift or fall off when a complex is made with the cellulose fiber and thereby, in which a synergistic effect can be expected in the water-absorbent performance.

To solve said object, the present invention provides a water absorbent matter made by containing a water-absorbent resin particle having an acidic group on the surface, a cellulose fiber, and a cationic high-molecular compound having a weight-average molecular weight of 2,000 or more. This water absorbent matter may be a mixture of the water-absorbent resin particle, cellulose fiber, and cationic high-molecular compound.

The present invention provides, to solve said object, a water absorbent matter made by containing a water absorbent and a cellulose fiber, the former of which is prepared by treating the water absorbent resin particle having an acidic group on the surface with a cationic high-molecular compound having a weight-average molecular weight of 2,000 or more. This water absorbent matter may be a mixture of a water absorbent and a cellulose fiber.

The present invention provides, to solve said object, a method for producing a water absorbent matter, which comprises mixing a water-absorbent resin particle having an acidic group on the surface, a cellulose fiber, and a cationic high-molecular compound having a weight-average molecular weight of 2,000 or more in a gas phase and then, pneumatically molding this mixture.

Furthermore, the present invention provides, to solve said object, a method for producing a water absorbent matter, which comprises mixing in a gas phase a water absorbent and a cellulose fiber, the former of which is made by treating a water-absorbent resin particle having an acidic group on the surface with a cationic high-molecular compound having a weight-average molecular weight of 2,000 or more and then, pneumatically molding this mixture.

To solve said object, the present invention provides a method for producing a water absorbent which comprises treating a surface of a water-absorbent resin particle having an acidic group with a crosslinking agent having two or more of a functional group capable of making a covalent bond by reacting with said acidic group and, thereby, crosslinking the surface by a part of said acidic group, then mixing the particle with a cationic high-molecular compound having a weight-average molecular weight of 2,000 or more which is capable of making an ionic bond by reacting with the acidic group.

Accordingly, the present invention provides the following four items: a water absorbent characterized by being composed of a water-absorbent crosslinked polymer and a polyamidopolyamine epihalohydrine resin; a method for producing a water absorbent characterized by mixing a polyamidopolyamine epihalohydrine resin with a water-absorbent crosslinked polymer; an absorbent matter composed of the water absorbent of this invention and a cellulose fiber; and a method for producing an absorbent matter characterized by mixing the water absorbent of this invention with a cellulose fiber in a dry condition and then, compressing an obtained mixture.

The water-absorbent resin usable in the present invention needs to have an acidic group. A preferable acidic group of this kind is, for example, a carboxyl group. Preferable examples of a water-absorbent resin having a carboxyl group on the surface are, for example, a crosslinked polyacrylate, a crosslinked copolymer of vinyl alcohol-acrylate, a crosslinked product of a starch-acrylate graft polymer, a crosslinked product of maleic anhydride graft polyvinyl alcohol, an alkali salt-crosslinked product of carboxymethylcellulose, etc. The amount of an acidic group involved in a water-absorbent resin has not any special limitation, but it is preferred that the acid group exists in 0.01 equivalent or more against 100 g of the water-absorbent resin. A preferable water-absorbent resin particle has been disclosed, for example, Japanese Official Patent provisional Publication, showa 57-34101; Japanese Official Patent Gazette, showa 58-35605; Japanese Official Patent Gazette, showa 62-16315; Japanese Official Patent Gazette, heisei 2-14361; Japanese Official Patent Provisional Publication, showa 62-144748; Japanese Official Patent Provisional Publication, showa 62-54751; Japanese Official Patent Provisional Publication, showa 63-21902. Particularly preferable one is a crosslinked polyacrylate particle having a neutralization degree of from about 50 to 95 mol % from a viewpoint of the water-absorbent performance. The polymerization method has not any special limitation.

The shape of the water-absorbent resin particle may be any one of a sphere type, a scale type, a pulverized amorphous type, a granule type, etc. Preferable size of the particle is in a range of from about 10 to 1000 $\mu m$ and more preferable one is in a range of from about 20 to 840 $\mu$ m. If there exist a particle having a size of less than 10 $\mu m$, gel blocking may occur when the water-absorbent resin particle in a water absorbent matter swells and, if there exist a particle having a size exceeding 1000 $\mu m$, the water absorbent matter may give a rugged feeling in using.

In the present invention, there may be used either a method of mixing a water absorbent and a cellulose fiber, the former of which is made by treating the surface of a water-absorbent resin particle beforehand with a cationic high-molecular compound, or a method of mixing a water absorbent resin particle, a cationic high-molecular compound, and a cellulose fiber without setting a process for treating the surface of the water absorbent resin particle beforehand, or a method of mixing a water absorbent resin particle and a cellulose fiber which has been treated beforehand by a cationic high molecular compound, and either of the methods can give similar effects.

A preferable cationic high-molecular compound used in the present invention is a compound capable of making an ionic bond by reacting with an acidic group such as a carboxyl group of the water-absorbent resin as well as a cationic high-molecular compound having a weight-average molecular weight of at least 2,000, and the one having a weight-average molecular weight of 5,000 or more is preferred and the one having a weight-average molecular weight of 10,000 or more is more preferred. A cationic high-molecular compound having a weight-average molecular weight of 2,000 or more used in the present invention is not limited with a compound showing a single maximum value (a peak) in a molecular weight analysis by gel permeation chromatography, and a compound having a weight-average molecular weight of 2,000 or more may be used even if it exhibits a plural maximum value (peaks). If a cationic high-molecular compound having a weight-average molecular weight of less than 2,000 is used, or if a cationic high-molecular compound is not used, but instead an anionic high-molecular compound or a nonionic high-molecular compound is used, firm fixing with a cellulose fiber is insufficient and, in absorbing water, shifting and falling-off of the water-absorbent resin may take place.

Preferable cationic high-molecular compounds used in the present invention are the compounds containing one kind selected from a primary amino group, a secondary amino group, a tertiary amino group, and their salts. In this case, the salts of an amino group mean a compound, of which nitrogen atom of the amino group is neutralized with an inorganic acid or an organic acid. An inorganic acid usable for this neutralization is, for example, hydrochloric acid, nitric acid, sulfuric acid, or phosphoric acid, etc. An organic acid usable here is, for example, formic acid, acetic acid, propionic acid, or p-toluenesulfonic acid, etc.

Practical examples of the cationic high-molecular compound are cationic polyelectrolytes that are, for example, polyethyleneimine, a modified polyethyleneimine which is crosslinked by epihalohydrine in a range soluble in water, polyamine, a modified polyamidoamine by graft of ethyleneimine, a protonated polyamidoamine, polyetheramine, polyvinylamine, modified polyvinylamine, polyalkylamine, polyamidopolyamine epihalohydrine, polyvinylimidazole, polyvinylpyridine, polyvinylimidazoline, polyvinyltetrahydropyridine, polydialkylaminoalkyl vinyl ether, polydialkylaminoalkyl (meth)acrylate, polyallylamine, and salts of these compounds.

A preferable amount of the cationic high-molecular compound is in a range of from about 0.1 to 30 parts by weight against 100 parts by weight of the water absorbent resin particle, a more preferable one is in a range of from about 0.3 to 20 parts by weight, and the most preferable is in a range of from about 0.5 to 10 parts by weight. If an amount of the cationic high-molecular compound is less than 0.1 part by weight, there is a case where an improvement of the water-absorbent resin is insufficient and, if it exceeds 30 parts by weight, there is a case where an effect corresponding to an added amount is not obtained, so that these cases are economically disadvantageous. The cationic high-molecular compound is water-soluble and it is used in form of powder or an aqueous solution, or in a form dissolved in a mixture solvent of water with a hydrophilic solvent such as ethanol or in a form allowed to react with the water absorbent resin particle.

For a purpose to include the cationic high-molecular compound in a water absorbent matter, if the cationic high-molecular compound can be arranged so as to become a binder of the water-absorbent resin particle with a cellulose fiber, a means to do so is not limited. The cationic high-molecular compound may be added in form of a powder, may be sprayed in a liquid form which is made by dissolving or dispersing it in a vehicle such as water or an organic solvent etc., or used in a method which comprises removing the vehicle after immersing in the forementioned liquid, if necessary, removing the vehicle by drying. A preferable method is such as mixing a water absorbent resin particle beforehand with a cationic high-molecular compound and thereby, obtaining a water-absorbent agent by treating the surface of the water absorbent resin particle, and furthermore, mixing the water-absorbent agent with a cellulose fiber in a dry condition. The mixing of a water-absorbent resin particle with a cationic high-molecular compound is carried out by using a device such as a high speed agitating mixer, an air mixer, a tumbling mixer, and bundary mixer. In mixing, it may be possible to coexist an organic powder such as a cellulose powder etc. and an inorganic powder such as silica fine particles etc. Furthermore, the water absorbent resin particle treated as the above may be, if necessary, dried.

The treatment of a water-absorbent resin particle with a cationic high-molecular compound is carried out, for example, by blending both the resin particle and the high-molecule compound in the presence of water and bringing them in contact during from 10 seconds to 60 minutes. Otherwise, a reaction of a water-absorbent resin particle with a cationic high-molecular compound can be allowed either by mixing the water-absorbent resin particles beforehand with the cationic high-molecular compound particles followed by adding water or an aqueous solution or by mixing beforehand the water-absorbent resin particles and cationic high-molecular compound particles with a cellulose fiber followed by adding water or an aqueous solution. In the latter case, the adding of water, etc. does not require to be in advance of the use of a water absorbent matter, but it is possible by water-absorption during the time of using the water absorbent matter. In this case, treatment of the water-absorbent resin particles with the cationic high-molecular compound and firm adhesion of the particles with the cellulose fiber occur simultaneously in the using time.

In the present invention, an aqueous solution containing a cationic high-molecular compound or water or an aqueous solution not containing a cationic high-molecular compound is mixed with water-absorbent resin particles in several types of form. For example, the water-absorbent resin particles may be immersed in a solution, mixed with liquid drops, or mixed in a mist type formed by spraying the solution.

The polyamidopolyamine epihalohydrine resin used in the present invention is, for example, a resin obtained from a condensation polymer between a polyalkylenepolyamine and a polycarboxylic acid by reacting with an epihalohydrine and, there is more practically exemplified a polyamidopolyamine epichlorohydrine resin obtained from a condensation product between diethylenetriamine and adipic acid by reacting with epichlorohydrine.

In the present invention, a preferable amount of a polyamidopolyamine epihalohydrine resin is in a range of from about 0.01 to 30 parts by weight against 100 parts by weight of a dried water-absorbent crosslinked polymer, a more preferable amount is in a range of from about 0.1 to 20 parts by weight, and the most preferable amount is in a range of from about 0.5 to 10 parts by weight. If it is less than 0.01 part by weight, improvement of the water-absorbent crosslinked polymer may be insufficient and, if it exceeds 30 parts by weight, an effect corresponding to an added amount may not be obtained and also, economically disadvantageous.

The water absorbent of present invention is obtained by adding followed by mixing a polyamidopolyamine epihalohydrine resin with a water-absorbent crosslinked polymer. The time for adding it to the water-absorbent crosslinked polymer is not especially limited as far as it does not disturb a process for producing a water absorbent and, for example, it is possible to add and mix a water-absorbent crosslinked polymer having a water-containing gel condition after drying of this polymer, after drying followed by crushing of it, or in a process for granulating it. In this case, it is preferred to carry out the mixing in the presence of water. Therefore, it is more preferred that the polyamidopolyamine epichlorohydrine resin is added and mixed with the water-absorbent crosslinked polymer under a condition of an aqueous solution. In the present invention, it is possible to add an aqueous solution containing a polyamidopolyamine epichlorohydrine resin under a mixing condition in form of an aqueous solution, a liquid drop, and a mist (a very small liquid drop), etc. Also, a hydrophilic organic solvent such as ethanol may be contained in an aqueous solution. In mixing a polyamidopolyamine epihalohydrine resin with a water-absorbent crosslinked polymer, there has been used a device, for example, a high speed agitating mixer, an air mixer, a trumbling mixer, and a bundary mixture, etc. In mixing, it is possible to coexist an organic powder such as a cellulose powder, etc. or an inorganic powder such as silica fine particles. Furthermore, the water absorbent obtained may be dried, if necessary.

To obtain a water absorbent matter from the forementioned water-absorbent resin particles (or water absorbent) and a cellulose fiber, there may be adopted a means known in public, for example, a method which comprises spreading water-absorbent resin particles on a paper or mat consisting of a cellulose fiber and then, if necessary, holding the particles with the paper or mat, and a method which comprises blending uniformly a cellulose fiber and water absorbent resin particles. A preferable means is a method which comprises mixing (that is, dry type mixing) water absorbent resin particles with a cellulose fiber in a gas phase followed by pneumatically molding an obtained mixture and compressing. It is possible by this method to greatly suppress falling-off of the water-absorbent resin particles from the cellulose fiber. The compressing may be carried out under heating and the temperature range is, for example, from about 50° to 200° C.

The cellulose fibers preferably usable in the present invention are, for example, a wood pulp fiber such as a mechanical pulp, chemical pulp, semichemical pulp, and dissolved pulp, and an artificial cellulose fiber such as rayon and acetate, etc. A preferable cellulose is a wood pulp fiber. These cellulose fibers may partly contain a synthetic fiber such as polyethylene, polypropylene, Nylon, a polyester, etc.

The water absorbent matter in the present invention can be composed of from 10 to 95% by weight of water absorbent resin particles and from 5 to 90% by weight of a cellulose fiber (a total of the water-absorbent resin particles and the cellulose fiber is 100% by weight). In particular, in a low proportion range of the cellulose fiber (for example, from 5 to 60% by weight), the weight of the water absorbent matter is as light as in a degree of from about one second to one third of a prior one (cellulose fiber proportion=80 to 90% by weight), but the absorbent matter displays a water-absorbent performance in an extent equal to or more than the prior one. The water absorbent matter of this invention has, for example, a density of from about 0.01 to 0.50 g/cm$^3$.

The water absorbent matter of the present invention is not limited by its shape and a distribution condition of each component existing in the water absorbent matter. Therefore, there can be adopted a method which is hitherto known in public and has been used to obtain a water absorbent matter having a shape suitable for using as a disposable diaper or a sanitary napkin, for example, of a sheet type or a web type.

Besides, in this invention the water-absorbent resin particles may be treated, for example, with a crosslinking agent to crosslink the surface by a covalent bond before treating with a cationic high-molecular compound. The present inventors found a new method for producing a water absorbent, which is superior in the water-absorbent properties as well as in the affinity with a cellulose fiber, in a process researching water absorbent matters of this invention. The water absorbent like this can be obtained from a method which comprises treating the particle surface of a water-absorbent resin having an acidic group with a crosslinking agent having two or more of a functional group capable of forming a covalent bond by reacting with said acidic group, thereby crosslinking the particles at a part of said acidic group, and then, mixing the particles with a cationic high molecular compound having a weight-average molecular weight of 2000 or more capable of forming an ionic bond by reacting with the acidic group. In this treatment, a layer crosslinked by a covalent bond should not be bonded with all of the acidic groups on the particle surface and it is necessary to retain a part of the acidic groups necessary for ionic crosslinking. A suitable amount for use of the crosslinking agent is in a range of from about 0.01 to 10 parts by weight against 100 parts by weight of a water-absorbent resin. If the crosslinking agent is less than 0.01 part by weight, the crosslinking may be insufficient and, if it exceeds 10 parts by weight, a remaining amount of the acidic groups capable of ionic bonding may be insufficient. In a process of forming a crosslinked layer by this covalent bond, it is important that an aqueous solution containing a crosslinking agent is used and mixed in an amount of not covering all of the surface of water-absorbent resin particles (for example, an amount such that a weight ratio of the crosslinking agent to a water absorbent matter is in the above-mentioned range). A mixture of the water-absorbent resin particles and the crosslinking agent is treated with heating at a temperature in a range of from about 40° to 250° C. for from 1 to 120 minutes and thereby, a layer crosslinked by a covalent bond is formed on the surface of water-absorbent resin particles. The mixing of an aqueous solution containing a crosslinking agent with the water-absorbent resin particles is carried out in various form (for example, by immersing the particles in an aqueous solution of a crosslinking agent, by mixing liquid drops of this aqueous solution with the particles, and by converting this aqueous solution in a mist type with spraying and then, mixing it with the particles). In this mixing, there has been used a device, for example, a high speed agitating mixer, an air mixer, a trumbling mixer, and a bundary mixture, etc. In mixing, it is possible to coexist an organic powder such as a cellulose powder, etc. or an inorganic powder such as silica fine particles. Water-absorbent resin particles after the treatment may be dried, if necessary.

The forementioned crosslinking agent has not any special limitation as far as it is a compound having two or more of a functional group capable of forming a covalent bond by reacting with an acidic group of the water-absorbent resin, and also, the two or more functional groups need not to be identical each other. Functional groups of this kind are, for example, an epoxy group, an aldehyde group, and a hydroxyl group. Preferable crosslinking agents are, for example, a polyglycidyl ether such as ethylene glycol diglycidyl ether, polyethylene glycol diglycidyl ether, glycerine triglycidyl ether, etc.; a haloepoxy compound such as epichlorohydrine and α-met hylchlorohydrine, etc.; a polyaldehyde such as glutaraldehyde (glutaric dialdehyde) and glyoxal, etc.; and a polyol such as glycerine, pentaerythritol, ethylene glycol, and polyethylene glycol, and they are used alone or in combination of two kinds or more. Preferable crosslinking agents are water-soluble and are used in form of an aqueous solution or in a form dissolved in a mixed solvent of water and a hydrophilic organic solvent such as ethanol.

In this invention, in case of carrying out both of treatment by using a crosslinking agent and treatment by using a cationic high-molecular compound, the sequence of these treatments is important. If a covalent bond-crosslinked layer is set after an ionic bond being set, or if both the layer is simultaneously set, the effects of this invention are not obtained. Also, if only the ionic bond layer is set without setting a covalent bond-crosslinked layer, or if only the covalent bond-crosslinked layer is set without setting an ionic bond layer, the effects of this invention are not similarly obtained. The water-absorbent matter of the present invention, even after the water-absorbent resin particles swelled by absorbing water, is little in falling-off from a cellulose fiber, in shifting in a cellulose fiber, and in decomposition of water-absorbent resin particles, and is superior in the water-absorbent property, so that it can be applied in various uses. The undermentioned are examples of the fields for use.

(1) Water absorbent matter used for absorbent articles disposable diaper, sanitary napkin, urinary incontinence pad, and pad for medical service, etc.

(2) Water-absorbent and water-holding matter used for agriculture and gardening sphagnum replacement, soil-improving material, water-holding material, and material by which the effects of agricultural chemicals, etc. last.

(3) Water absorbent matter for architecture dew condensation-preventive material for interior decorating wall material, and cement-curing material, etc.

(4) Others release-controlling material, material to maintain the cold, disposable body warmer, material for sludge-solidification, material to maintain freshness for foods, and drip-absorbent material, etc.

If there are contained a cationic high-molecular compound, water-absorbent resin particles, and a cellulose fiber in the presence of water, the cationic high-molecular compound works like a binder of the water-absorbent resin particles with the cellulose fiber, so that the water-absorbent resin particles are firmly set with the cellulose fiber via the cationic high-molecular compound. By being set like this, the water-absorbent resin particles does not easily shift in the cellulose fiber or fall off from the cellulose fiber, even when it has absorbed water. Besides, decomposition of the water-absorbent resin is prevented.

The surface of water-absorbent resin particles having acidic groups is treated with a crosslinking agent having two or more of a functional group capable of making a covalent bond by reacting with the acidic groups, thereby crosslinking is carried out at a part of the acidic groups, thereby the water-absorbent resin particles becomes hard in forming fish-eyes and the water-absorbent performance of water-absorbent resin itself is elevated. Besides, after treating with a crosslinking agent, the surface of particles is mixed with a cationic high-molecular compound capable of making an ionic bond by reacting with the acidic group. The cationic high-molecular compound undergoes a reaction with the acidic group remaining on the particle surface in the presence of water and, in the presence of water, it makes easy the water-absorbent resin particles in putting together with a partner material such as a cellulose fiber, which makes a complex [to make the putting-together easy is possible not only by liquid water, but also by water in a gas phase (so-called moisture)]. By doing these, even after absorbing water, it becomes difficult that the water-absorbent resin shifts in the partner material for making a complex such as a cellulose fiber or it falls off from the material. This kind of effects is only possible by carrying out the above treatment in the forementioned sequence.

The water absorbent matter of this invention shows superior effects such as no falling-off and no shifting of swelled water-absorbent resin particles. The shifting aside etc. which is liable to occur after absorption of a solution in a conventional water absorbent matter is much improved in the water absorbent matter of this invention.

Accordingly, the water absorbent matter of this invention is very useful for an absorption article such as a disposable diaper, sanitary napkin, and an urinary inconvenience pad. Such a superior water-absorbent matter is easily produced according to the production method of this invention.

According to the method for producing a water absorbent of this invention, there is obtained a water absorbent which displays a superior water-absorbent property in a sole use. Besides, this water absorbent has such a superior effect as, in a case where the absorbent was led to a water absorbent matter by making a complex with a cellulose fiber, it does not fall off or does not shift even after absorbing water or swelling. Since shifting and falling-off of the water absorbent in this water absorbent matter are little even after absorbing water, the shifting aside of a water absorbent matter which is hitherto liable to occur is much improved. Accordingly, the water absorbent obtained from the present invention is particularly useful for water-absorbent articles such as disposable diapers, sanitary napkins, and urnary incontinence pads.

A water absorbent of the present invention has not only an effect that it displays a superior water-absorbent property in a sole use, but also a superior effect that the water absorbent does not fall off or does not shift even after swelling, for example, in a case where the absorbent is led to a water absorbent matter by making a complex with a cellulose fiber. Since shift and falling-off of the water absorbent are little even after absorbing liquid, the water absorbent matter of the present invention is able to greatly improve the shifting aside of a water absorbent matter which is so far liable to occur. Accordingly, a water absorbent and a water absorbent matter obtained from the present invention are particularly useful for water-absorbent articles such as disposable diapers, sanitary napkins, and urnary incontinence pads.

DESCRIPTION OF THE PREFERRED EMBODIMENTS

Figure 1:
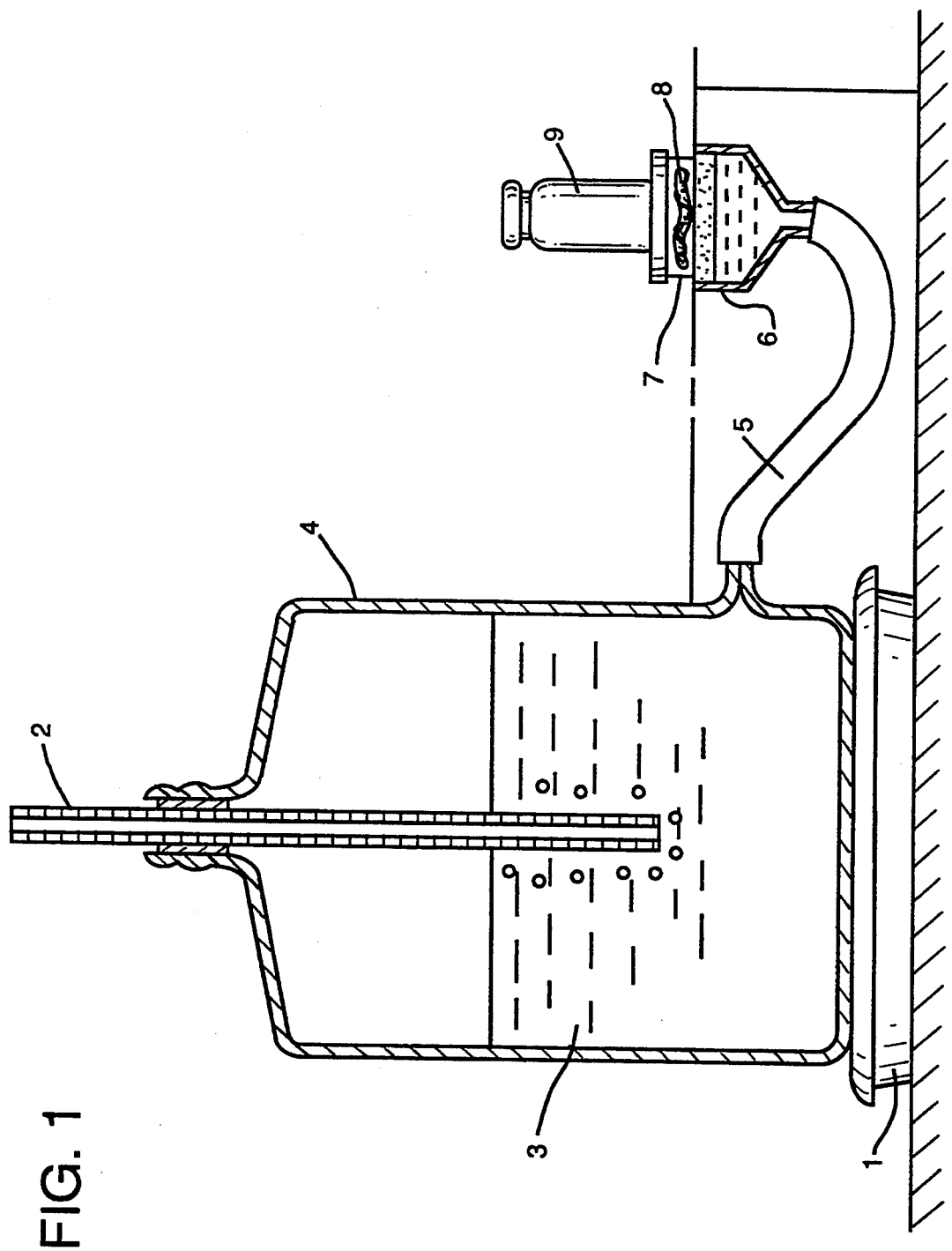
FIG. 1 is a schematic view of a device for measuring the absorption amount under pressure of a water absorbent matter.

Hereinafter, practical examples and comparative examples of the present invention are shown, but this invention is not limited with the undermentioned examples. Hereinafter, the simple denotations ⌞ % ⌟ and ⌜ part ⌟ mean ⌜ % by weight ⌟ and ⌜ part by weight ⌟ respectively.

Example for Synthesizing Water-Absorbent Resin

A polymerization reaction of 4,000 parts of a 37% aqueous solution of an acrylate-based monomer, composed of 74.95 mole % of sodium acrylate, 25 mole % of acrylic acid, 0.05 mole % of trimethylolpropane triacrylate, with 2.0 parts of ammonium persulfate and 0.08 parts of 1-ascorbic acid was carried out at a temperature in a range of from 30° to 80° C. under a nitrogen atmosphere, whereby a gel type water-containing crosslinked polymer was obtained. The polymer obtained is dried by a hot wind drier of 150° C. crushed by a hammer mill, and sieved by a 20 mesh metal net screen (a Tyler standard screen scale sieve, hereinafter the same), whereby a product which passed through the 20 mesh was obtained. This is called as the water-absorbent resin particles (a).

Production Example 1

To 100 parts of the water-absorbent resin particles (a) were added 0.5 parts of glycerine, 2 parts of water, and 2 parts of ethyl alcohol and mixed, and then the mixture was treated with heating at 210° C. for 10 minutes, whereby a water-absorbent polymer A secondary-cross linked at a part adjacent to the surface was obtained. Furthermore, to 100 parts of the water-absorbent polymer A obtained were added 20 parts of Polymine SK (a modified polyethyleneimine, made by BASF Co., Ltd., a weight-average molecular weight was about 100,000 and a 20% aqueous solution) and mixed then the mixture was dried with heating for 120° C. for 10 minutes and sieved by a 20 mesh screen, whereby a product which passed through the 20 mesh was obtained. This is called as the water absorbent (1-1).

Production Example 2

With 100 parts of the water-absorbent polymer A obtained from the production example 1 were mixed by spraying 15 parts of Polymine SN (a modified polyethyleneimine, made by BASF Co., Ltd., a weight-average molecular weight was about 100,000, and a 20% aqueous solution), and then the mixture was dried with heating for 120° C. for 10 minutes and sieved by a 20 mesh screen, whereby a product which passed through the 20 mesh was obtained. This is called as the water absorbent (1-2).

Production Example 3

To 100 parts of the water-absorbent polymer A obtained from the production example 1 were added 5 parts of a 30% aqueous solution of Epomine P-1000 (a polyethyleneimine, made by Nippon Shokubai Co., Ltd., a weight-average molecular weight was about 70,000) and mixed, whereby a water absorbent (1-3) were obtained.

Production Example 4

To 100 parts of the water-absorbent resin particles (a) were added 33.4 parts of a 30% aqueous solution of Epomine P-1000 (a polyethyleneimine, made by Nippon Shokubai Co., Ltd., a weight-average molecular weight was about 70,000) and mixed, then the mixture obtained was dried with heating at 120° C. for 20 minutes and sieved by a 20 mesh screen, whereby a product which passed through the 20 mesh was obtained. This is called as the water absorbent (1-4).

Production Example 5

To 100 parts of the water-absorbent polymer A obtained from the production example 1 were added 1.7 parts of a 30% aqueous solution of Epomine P-1000 (a polyethyleneimine, made by Nippon Shokubai Co., Ltd., a weight-average molecular weight was about 70,000) and mixed, whereby a water absorbent (1-5) were obtained.

Production Example 6

100 parts of the water-absorbent polymer A obtained from the production example 1 were added 10 parts of a 30% aqueous solution of Epomine SP-200 (a polyethyleneimine, made by Nippon Shokubai Co., Ltd., a weight-average molecular weight was about 10,000) and mixed, then the mixture obtained was dried with heating at 120° C. for 20 minutes and sieved by a 20 mesh screen, whereby particles which passed through the 20 mesh were obtained. This is called as the water absorbent (1-6).

Production Example 7

To 100 parts of the water-absorbent resin particles (a) were added 8 parts of a 10% aqueous solution of ethyleneglycol diglycidyl ether (Denacol EX-810, made by Nagase Chemicals Co., Ltd.) and mixed, then the mixture obtained was treated with heating at 120° C. for 30 minutes, whereby a water-absorbent polymer B secondary-crosslinked at a part adjacent to the surface was obtained. The water-absorbent polymer B was a powder. Furthermore, to 100 parts of the water-absorbent polymer thus-obtained B were added 3 parts of a dimethylaminoethyl acrylate-acrylamide-acrylic acid copolymer powder (a 30:60:10 mole ratio of dimethylaminoethyl acrylate to acrylamide to acrylic acid, a weight-average molecular weight was about 1,000,000, and a product which passed through a 100 mesh screen) and mixed, whereby a water absorbent (1-7) were obtained.

Production Example 8

The water-absorbent polymer A obtained from the production example 1 were led to a water-absorbent polymer C (a particle diameter of 250–149 μm) by classifying the polymer A with a 60–100 mesh screen. Then, to 100 parts of the water-absorbent polymer C were added 10 parts of a 30% solution of Epomine P-1000 (a polyethyleneimine, made by Nippon Shokubai Co., Ltd., a weight-average molecular weight was about 70,000) and mixed, dried with heating at 120° C. for 10 minutes, and sieved with a 20 mesh screen, whereby a product which passed through the 20 mesh was obtained. This is called as the water absorbent (1-8)

Production Example 9

The water-absorbent polymer A obtained from the production example 1 were led to a water-absorbent polymer D (a particle diameter of 149 μm or less) by classifying the polymer A with a 100 mesh screen. Then, to 100 parts of the obtained water-absorbent polymer D were added 10 parts of a 30% aqueous solution of Epomine P-1000 (a polyethyleneimine, made by Nippon Shokubai Co., Ltd., a weight-average molecular weight was about 70,000) and mixed, dried with heating at 120° C. for 10 minutes, and sieved with a 20 mesh screen, whereby a product which passed through the 20 mesh was obtained. This is called as the water absorbent (1-9).

Production Example 10

To 100 part of the water-absorbent polymer A obtained from the production example 1 were added 7.5 parts of a 40% aqueous solution of a polyallylamine hydrochloride salt PAA-HCL-10L, made by Nitto Boseki Co., Ltd., a weight-average molecular weight was about 60,000) and mixed, dried with heating at 120° C. for 10 minutes, and sieved with a 20 mesh screen, whereby a product which passed through the 20 mesh was obtained. This is called as the water absorbent (1-10).

Production Example 11

To 100 parts of the water-absorbent resin particles (a) were added 10 parts of a 30% aqueous solution of Epomine P-1000 (a polyethyleneimine, made by Nippon Shokubai Co., Ltd., a weight-average molecular weight was about 70,000) and mixed, dried with heating at 120° C. for 10 minutes, and sieved with a 20 mesh screen, whereby a product which passed through the 20 mesh was obtained. This is called as the water absorbent (1-11).

Production Example 12

To 100 part of the water-absorbent polymer A obtained from the production example 1 were added 12.5 parts of a 40% aqueous solution of a polyethyleneimine-polyethylene glycol block copolymer (a mole ratio between ethyleneimine and ethylene glycol was 50 to 50 and a weight-average molecular weight was about 80,000) and mixed, dried with heating at 120° C. for 10 minutes, and sieved with a 20 mesh screen, whereby a product which passed through the 20 mesh was obtained. This is called as the water absorbent (1-12).

Production Example 13

To 100 parts of the water-absorbent polymer A obtained from the production example 1 were added 20 parts of a 30% aqueous solution of Epomine P-1000 (a polyethyleneimine, made by Nippon Shokubai Co., Ltd., a weight-average molecular weight was about 70,000) and mixed, and the mixture obtained was dried with heating at 120° C. for 10 minutes and sieved by a 20 mesh screen, whereby a product passed through the 20 mesh was obtained, and then, 1.0 part of Aerosil 200 (fine silicone dioxide powder, made by Nippon Aerosil Co.) was added into the treated polymer with mixing. This is called as the water absorbent (1-13).

Comparative Production Example 1

The water-absorbent resin particles (a) were assigned as the comparative water absorbent (1-1).

Comparative Production Example 2

The water-absorbent polymer A obtained from the production example 1 was sieved by a 20 mesh screen to obtain a passed product. This is called as the comparative water absorbent (1-2).

Comparative Production Example 3

To 100 parts of the water-absorbent polymer A obtained from the production example 1 were added 10 parts of a 30% aqueous solution of ethylenediamine and mixed, and the mixture obtained was treated with heating at 120° C. for 10 minutes and sieved by a 20 mesh screen, whereby a product passed through the 20 mesh was obtained. This is called as the comparative water absorbent (1-3).

Comparative Production Example 4

To 100 parts of the water-absorbent polymer A obtained from the production example 1 were added 10 parts of a 30% solution of Epomine SP-012 (polyethyleneimine, made by Nippon Shokubai Co., Ltd., a weight-average molecular weight was about 1,200) and mixed, and the mixture obtained was dried with heating at 120° C. for 10 minutes and sieved by a 20 mesh screen, whereby a product passed through the 20 mesh was obtained. This is called as the comparative water absorbent (1-4).

Comparative Production Example 5

To 100 parts of the water-absorbent polymer A obtained from the production example 1 were added 3 parts of the N-100 powder (a nonionic acrylamide-based polymer having a weight-average molecular weight of about 17,000,000, made by Mitsui-Cyanamid, Ltd., a product which passed through a 100 mesh screen) and mixed. This is called as the comparative water absorbent (1-5).

Comparative Production Example 6

To 100 parts by weight of the water-absorbent crosslinked polymer (a) was added with mixing a mixture solution composed of 10 parts by weight of water and 2 parts by weight of an epichlorohydrin-ethylenediamine reaction solution (a product obtained by mixing with stirring 3 parts by weight of epichlorohydrin, 0.49 parts by weight of ethylenediamine, and 30 parts by weight of methanol followed by standing them at 50° C. for 15 hours for reaction, a weight-average molecular weight was about 980), whereby the comparative water absorbent (1-6) was obtained.

Example 1-1

The water absorbent (1-1), 100 parts, obtained from the production example 1, and 100 parts of ground pulp were mixed under a dry condition in a mixer and then, the produced mixture was pneumatically molded on a wire screen using a batch type pneumatically molding device, whereby a web having a size of 10 cm×20 cm was obtained. The upper and lower faces of the obtained web were held between tissue papers having a basis weight of 0.0013 g/cm$^2$ and pressed with heating for 1 minute at 150° C. under a pressure of 2 kg/cm$^2$, whereby the water absorbent matter (1-1) of this invention having a basis weight of about 0.05 g/cm$^2$ and a density of about 0.17 g/cm$^3$ was obtained.

Examples 1-2 to 1-13 and Comparison Examples 1-1 to 1-6

Using the water absorbent (1-2) to (1-13) obtained from the production examples 2 to 13 and the comparative water absorbent (1-1) to (1-6) obtained from the comparative production examples 1 to 6, the procedure of example 1-1 was repeated to obtain the water absorbent matters (1-2) to (1-13) and the comparative water absorbent matters (1-1) to (1-6). The water absorbent matters and water absorbents were denoted so as to have the same number.

Example 1-14

The water absorbent (1-11), 100 parts, obtained from the production example 11 and 100 parts of ground pulp were mixed under a dry condition in a mixer and then, the produced mixture was pneumatically molded on a wire screen using a batch type pneumatically molding device, whereby a web having a size of 10 cm×20 cm was obtained. The upper and lower faces of the obtained web were held between tissue papers having a basis weight of 0.0013 g/cm$^2$ and pressed for 1 minute at room temperature under a pressure of 2 kg/cm$^2$, whereby the water absorbent matter (1-14) of this invention having a basis weight of about 0.05 g/cm$^2$ and a density of about 0.07 g/cm$^2$ was obtained.

Example 1-15

The water absorbent (1-3), 20 parts, obtained from the production example 3 and 180 parts of ground pulp were mixed under a dry condition in a mixer and then, the produced mixture was pneumatically molded on a wire screen using a batch type pneumatically molding device, whereby a web having a size of 10 cm×20 cm was obtained. The upper and lower faces of the obtained web were held between tissue papers having a basis weight of 0.0013 g/cm$^2$ and pressed with heating for 1 minute at 150° C. under a pressure of 2 kg/cm$^2$, whereby the water absorbent matter (1-15) of this invention having a basis weight of about 0.05 g/cm$^2$ and a density of about 0.12 g/cm$^2$ was obtained.

Comparative Example 1-7

The procedure of example 1-15 was repeated except that the comparative water absorbent (1-2) obtained from the comparative production example 2 were used instead of the water absorbent (1-3), whereby a comparative water absorbent matter (1-7) having a basis weight of about 0.05 g/cm$^2$ and a density of about 0.12 g/cm$^2$ was obtained.

Example 1-16

The water absorbent (1-3), 40 parts, obtained from the production example 3 and 160 parts of ground pulp were mixed under a dry condition in a mixer and then, the produced mixture was pneumatically molded on a wire screen using a batch type pneumatically molding device, whereby a web having a size of 10 cm×20 cm was obtained. The upper and lower faces of the obtained web were held between tissue papers having a basis weight of 0.0013 g/cm$^2$ and pressed with heating for 1 minute at 150° C. under a pressure of 2 kg/cm$^2$, whereby the water absorbent matter (1-16) of this invention having a basis weight of about 0.05 g/cm$^2$ and a density of about 0.14 g/cm$^3$ was obtained.

Example 1-17

Into 100 parts of ground pulp were immersed 750 parts of a 0.4% aqueous solution of Epomine P-1000 (a polyethyleneimine having an average molecular weight of about 70,000, made by Nippon Shokubai Co., Ltd.). A matter obtained by drying the above-treated pulp with heat at 120° C. was mixed in a mixer and a dry condition with 100 parts of the water absorbent polymer A obtained from the production example 1, and the mixture obtained was pneumatically molding on a wire screen using a batch type pneumatically molding device, whereby a web having a size of 10 cm×20 cm was obtained. The upper and lower faces of the obtained web were held between tissue papers having a basis weight of 0.0013 g/cm$^2$ and pressed for 1 minutes at room temperature under a pressure of 2 Kg/cm$^2$, whereby the water absorbent matter (1-17) of this invention having a basis weight of about 0.05 g/cm$^2$ and a density of about 0.07 g/cm$^3$ was obtained.

Examples 1-18 to 1-34 and Comparative Examples 1-8 to 1-14

The water absorbent matters (1-1) to (1-17) obtained from the examples 1-1 to 1-17 and the comparative water absorbent matters (1-1) to (1-7) obtained from the comparative examples 1-1 to 1-7 were tested by the undermentioned methods to evaluate absorption properties of the water absorbent matters.

Amount of Absorption Under Pressure

As shown in FIG. 1, a device used was equipped with the open air-sucking pipe 2 placed on the scale 1, a vessel 4 which accommodates a 0.9% normal saline solution 3, and a reversed funnel 6 penetrated by a pipe 5 to a part of the vessel 4 which accommodates a normal saline solution, and furthermore, a plate 7 (a hole-opened plate) furnished with a liquid-supplying hole of a 10 mm diameter was fixed at the center of a top part of the reversed funnel 6. On the hole-opened plate 7 the water absorbent matter was placed, on which a weight 9 was placed, and after this weighting condition for 30 minutes using a 30 g/cm² load, an absorbing amount by the water absorbent matter (an absorption amount under pressure) was measured. Besides, the water absorbent matter used was such as being beforehand cut off in a circle of 9 cm diameter.

Falling-Off Percentage of Water Absorbent

Into 100 cc of a normal saline solution in a 100 cc beaker was poured a water absorbent matter being cut off in a 2 cm×4 cm size with stirring (using a 45 mm stirrer with 100 rpm stirring). After stirring for 10 minutes, the water absorbent matter was taken out, weight of the water absorbent matter fallen off in the normal saline solution was measured and a falling-off percentage of the water absorbent matter was determined. Besides, the amount of a water absorbent in the following equation (1) corresponds to a total amount of the water-absorbent resin and the cationic high-molecular compound.

Falling-off percentage (%) = 
$$\frac{\text{amount of water absorbent fallen off (g)}}{\text{amount of water absorbent in original water absorbent matter (g)}} \times 100$$ 
Equation 1

TABLE 1

| | No. of water absorbent | number | water absorbent matter absorption amount under pressure (g/g) | falling-off percentage of water-absorbent resin (%) |
|---|---|---|---|---|
| example 1-1 | (1-1) | (1-1) | 15.1 | 1 |
| example 1-2 | (1-2) | (1-2) | 15.6 | 1 |
| example 1-3 | (1-3) | (1-3) | 16.0 | 5 |
| example 1-4 | (1-4) | (1-4) | 15.0 | 1 |
| example 1-5 | (1-5) | (1-5) | 15.8 | 10 |
| example 1-6 | (1-6) | (1-6) | 15.5 | 26 |
| example 1-7 | (1-7) | (1-7) | 16.2 | 30 |
| example 1-8 | (1-8) | (1-8) | 16.3 | 25 |
| example 1-9 | (1-9) | (1-9) | 15.2 | 28 |

TABLE 1-continued

| | No. of water absorbent | number | water absorbent matter absorption amount under pressure (g/g) | falling-off percentage of water-absorbent resin (%) |
|---|---|---|---|---|
| example 1-10 | (1-10) | (1-10) | 15.4 | 2 |
| example 1-11 | (1-11) | (1-11) | 15.0 | 1 |
| example 1-12 | (1-12) | (1-12) | 15.1 | 19 |
| example 1-13 | (1-13) | (1-13) | 15.7 | 6 |
| example 1-14 | (1-11) | (1-14) | 15.2 | 1 |
| example 1-15 | (1-3) | (1-15) | 7.8 | 5 |
| example 1-16 | (1-3) | (1-16) | 10.5 | 18 |
| example 1-17 | — | (1-17) | 15.6 | 1 |

TABLE 2

| | No. of comparative water absorbent | number | comparative water absorbent matter absorption amount under pressure (g/g) | falling-off percentage of water-absorbent resin (%) |
|---|---|---|---|---|
| comparative example 1-1 | (1-1) | (1-1) | 15.2 | 96 |
| comparative example 1-2 | (1-2) | (1-2) | 16.1 | 92 |
| comparative example 1-3 | (1-3) | (1-3) | 15.0 | 93 |
| comparative example 1-4 | (1-4) | (1-4) | 15.0 | 82 |
| comparative example 1-5 | (1-5) | (1-5) | 15.0 | 100 |
| comparative example 1-6 | (1-6) | (1-6) | 12.3 | 97 |
| comparative example 1-7 | (1-2) | (1-7) | 7.8 | 83 |

As clearly seen in Tables 1 and 2, a water absorbent matter, in which a water absorbent obtained from a production method of the present invention is used, is superior in an absorption amount under pressure and much improved in the falling-off percentage of the water absorbent.

Example 2-1

To 100 parts of the water-absorbent polymer A obtained from the production example 1 were added 20 parts of Polymine SK (a modified polyethyleneimine, made by BASF Co., Ltd., a weight-average molecular weight was about 100,000, and a 20 % aqueous solution) and mixed, then the mixture was dried with heating at 120° C. for 10 minutes and sieved by a 20 mesh screen, whereby a product which passed through the 20 mesh was obtained. This is called as the water absorbent (2-1).

Example 2-2

To 100 parts of the water-absorbent polymer A obtained from the production example 1 were added 5 parts of a 30% aqueous solution of Epomine P-1000 (a polyethyleneimine, made by Nippon Shokubai Co., Ltd., a weight-average molecular weight was about 70,000) and mixed, whereby a water absorbent (2-2) were obtained. The water absorbent (2-2) was a powder.

Example 2-3

To 100 parts of the water-absorbent polymer A obtained from the production example 1 were added 1.7 parts of a 30% aqueous solution of Epomine P-1000 (a polyethyleneimine, made by Nippon Shokubai Co., Ltd., a weight-average molecular weight was about 70,000) and mixed, whereby a water absorbent (2-3) were obtained. The water absorbent (2-3) was a powder.

Example 2-4

To 100 parts of the water-absorbent polymer A obtained from the production example 1 were added 10 parts of a 30% aqueous solution of Epomine SP-200 (a polyethyleneimine, made by Nippon Shokubai Co., Ltd., a weight-average molecular weight was about 10,000) and mixed, and the mixture obtained was dried with heating at 120° C. for 20 minutes and sieved by a 20 mesh screen, whereby a product passed through the 20 mesh was obtained. This is called as the water absorbent (2-4).

Example 2-5

To 100 parts of the water-absorbent resin particles (a) were added 8 parts of a 10% aqueous solution of ethyleneglycol diglycidyl ether (DenacoL EX-810, made by Nagase Chemicals Co., Ltd.) and mixed, then the mixture obtained was treated with heating at 120° C. for 30 minutes, whereby a water-absorbent polymer B secondary-crosslinked at a part adjacent to the surface was obtained. The water-absorbent polymer B was a powder. Furthermore, to 100 parts of the water-absorbent polymer thus-obtained B were added 3 parts of a dimethylaminoethyl acrylate-acrylamide-acrylic acid copolymer powder (a 30:60:10 mole ratio of dimethylaminoethyl acrylate to acrylamide to acrylic acid, a weight-average molecular weight was about 1,000,000, and a product which passed through a 100 mesh screen) and mixed, whereby a water absorbent (2-5) were obtained.

Example 2-6

To 100 part of the water-absorbent polymer A obtained from the production example 1 were added 7.5 parts of a 40% aqueous solution of a polyallylamine hydrochloride salt PAA-HCL-10L, made by Nitto Boseki Co., Ltd., a weight-average molecular weight was about 60,000) and mixed, dried with heating at 120° C. for 10 minutes, and sieved with a 20 mesh screen, whereby a product which passed through the 20 mesh was obtained. This is called as the water absorbent (2-6).

Example 2-7

To 100 parts of the water-absorbent polymer A obtained from the production example 1 were added 12.5 parts of a 40% aqueous solution of polyethyleneimine polyethylene glycol block copolymer (a 50:50 mole ratio of ethyleneimine to ethylene glycol, a weight-average molecular weight was about 80,000) and mixed, and the mixture obtained was dried with heating at 120° C. for 10 minutes and sieved by a 20 mesh screen, whereby a product passed through the 20 mesh was obtained. This is called as the water absorbent (2-7)

Example 2-8

To 100 parts of the water-absorbent polymer A obtained from the production example 1 were added 20 parts of a 30% aqueous solution of Epomine P-1000 (a polyethyleneimine, made by Nippon Shokubai Co., Ltd., a weight-average molecular weight was about 70,000) and mixed, and the mixture obtained was dried with heating at 120° C. for 10 minutes and sieved by a 20 mesh screen, whereby a product passed through the 20 mesh was obtained. This is called as the water absorbent (2-8).

Comparative Example 2-1

The water-absorbent resin particles (a) were assigned as the comparative water absorbent (2-1).

Comparative Example 2-2

The water-absorbent polymer A obtained from the production example 1 was sieved by a 20 mesh screen to obtain a passed product. This is called as the comparative water absorbent (2-2).

Comparative Example 2-3

To 100 parts of the water-absorbent polymer A obtained from the production example 1 were added 10 parts of a 30% aqueous solution of ethylenediamine and mixed, and the mixture obtained was treated with heating at 120° C. for 10 minutes and sieved by a 20 mesh screen, whereby a product passed through the 20 mesh was obtained. This is called as the comparative water absorbent (2-3).

Comparative Example 2-4

To 100 parts of the water-absorbent polymer A obtained from the production example 1 were added 10 parts of a 30% aqueous solution of Epomine SP-012 (polyethyleneimine, made by Nippon Shokubai Co., Ltd., a weight-average molecular weight was about 1,200) and mixed, and the mixture obtained was dried with heating at 120° C. for 10 minutes and sieved by a 20 mesh screen, whereby a product passed through the 20 mesh was obtained. This is called as the comparative water absorbent (2-4).

Comparative Example 2-5

To 100 parts of the water-absorbent polymer A obtained from the production example 1 were added 3 parts of the N-100 powder (a nonionic acrylamide-based polymer having a weight-average molecular weight of about 17,000,000, made by Mitsui-Cyanamid, Ltd., a product which passed through a 100 mesh screen) and mixed. This is called as the comparative water absorbent (2-5).

Comparative Example 2-6

To 100 parts of the water-absorbent resin particles (a) were added 33.4 parts of a 30% aqueous solution of Epomin P-1000 (a polyethyleneimine having a weight-average molecular weight of about 70,000, made by Nippon Shokubai Co., Ltd.) and mixed, the mixture obtained was dried with heating at 120° C. for 20 minutes and sieved by a 20 mesh screen, whereby a product passed through the 20 mesh was obtained. This is called as the comparative water absorbent (2-6).

Comparative Example 2-7

To 100 parts of the water-absorbent resin particles (a) were added 10 parts of a 30% aqueous solution of Epomin P-1000 (a polyethyleneimine having a weight-average molecular weight of about 70,000, made by Nippon Shokubai Co., Ltd.) and mixed, the mixture obtained was dried with heating at 120° C. for 10 minutes, to which were added 0.5 parts of glycerine, 2 parts of water, and 2 parts of ethyl alcohol and the mixture obtained was heated at 210° C. and sieved by a 20 mesh screen, whereby a product passed through the 20 mesh was obtained. This is called as the comparative water absorbent (2-7).

Example 2-9 to 2-16 Comparative Examples 2-8 to 2-14

Water-absorbent properties of the water absorbents (2-1) to (2-8) obtained from the examples 2-1to 2-8 and the comparative water absorbents (2-1) to (2-7) obtained from the comparative examples 2-1to 2-7 were compared by the under-described methods. Results obtained are shown in Table 3.

Water Absorbency

A water absorbent, about 0.2 g, was uniformly put into tea-bag type pouch (40 mm×150 mm) made of a nonwoven fabric, immersed in an large excess of a normal saline solution (a 0.9% sodium chloride solution), and stood for 30 minutes. By doing these, the water absorbent in the pouch converted into a swelled gel. The tea-bag type which accommodated this swelled gel was drained and then, weighed. The water-absorbed weight by only the tea-bag type pouch was taken as a blank and, a value obtained by deducing the blank weight from the weight of after water-absorption was divided by the weight of water absorbent, and a thus-obtained value was assigned as the water absorbency (g/g).

Suction Power

A water absorbent, 1 g, was added onto 16 sheets of toilet papers (55 mm×75 mm) which had been immersed in 20 ml of artificial urine (composition: an aqueous solution containing 1.9% of urea, 0.8% of sodium chloride, 0.1% of calcium chloride, and 0.1% of magnesium sulfate), and a solution was absorbed during 10 minutes and then, a swelled gel was taken, of which weight was defined as the suction power (g/g).

TABLE 3

(part 1/2)

| | water absorbent | | |
|---|---|---|---|
| | number | water absorbancy (g/g) | suction power (g/g) |
| example 2-1 | (2-1) | 42 | 14.5 |
| example 2-2 | (2-2) | 45 | 14.6 |
| example 2-3 | (2-3) | 44 | 15.2 |
| example 2-4 | (2-4) | 42 | 14.7 |
| example 2-5 | (2-5) | 44 | 17.2 |
| example 2-6 | (2-6) | 40 | 16.0 |
| example 2-7 | (2-7) | 45 | 14.4 |
| example 2-8 | (2-8) | 42 | 16.3 |

(part 2/2)

| | comparative water absorbent | | |
|---|---|---|---|
| | number | water absorbancy (g/g) | suction power (g/g) |
| comparative example 2-1 | (2-1) | 44 | 12.9 |
| comparative example 2-2 | (2-2) | 45 | 16.0 |
| comparative example 2-3 | (2-3) | 40 | 15.1 |
| comparative example 2-4 | (2-4) | 41 | 15.0 |
| comparative example 2-5 | (2-5) | 44 | 15.6 |
| comparative example 2-6 | (2-6) | 43 | 13.6 |
| comparative example 2-7 | (2-7) | 44 | 13.4 |

As seen in Table 3, the water absorbents obtained from the present examples show high water absorbency and high suction power. The suction power is an index for the water absorption velocity and, that it is high means a high water absorption velocity. Among the water absorbents obtained from the comparative examples, those obtained from the comparative examples 2-2 to 2-5 show water absorbency and suction power similar to those obtained from the examples. However, in the comparative example 2-1 the water-absorbent resin particles (a) showed a low suction power because of no treatment, in the comparative example 2-6 the suction power was low because of no crosslinking by a crosslinking agent, and in the comparative example 2-7, because the crosslinking was attempted by a crosslinking agent after treating with a cationic high-molecular compound and, thereby, it was not sufficiently carried out and, as a result, the suction power was low.

Example 2-17

The water absorbent (2-1), 100 parts, obtained from the example 2-1 and 100 parts of ground pulp were mixed under a dry condition in a mixer and then, the produced mixture was pneumatically molded on a wire screen using a batch type pneumatically molding device, whereby a web having a size of 10 cm×20 cm was obtained. The upper and lower faces of the obtained web were held between tissue papers having a basis weight of 0.0013 g/cm$^2$ and pressed for 1 minute under a pressure of 2 kg/cm$^2$, whereby the water absorbent matter (2-1) having a basis weight of about 0.05 g/cm$^2$ was obtained.

Examples 2-18 to 2-24 and Comparative Examples 2-15 to 2-18

Using the water absorbents (2-2) to (2-8) obtained from the examples 2-2 to 2-8 and the comparative water absorbents (2-2) to (2-5) obtained from the comparative examples 2-2 to 2-5 in which the water absorbency and suction power were similar to those in the examples, the procedure of example 2-17 was carried out to obtain the water absorbent matters (2-2) to (2-8) and comparative water absorbent matters (2-1) to (2-4). Besides, in the examples the water absorbent matters and water absorbents were denoted so as to have the same number, and in the comparative examples, the number of comparative water absorbent matters was afforded in sequence of from a comparative water absorbent having a low number to that having a high number.

Examples 2-25 to 2-32 and Comparative Examples 2-19 to 2-22

The water absorbent matters (2-1) to (2-8) obtained from the examples 2-17 to 2-24 and the comparative water absorbent matters (2-1) to (2-4) obtained from the comparative examples 2-15 to 2-18 were tested by the above-mentioned methods to evaluate absorption properties of the water absorbent matters. Results obtained are shown in Table 4.

TABLE 4

(part 1/2)

| | water absorbent matter | |
|---|---|---|
| No. of water | absorption amount under pressure | falling-off percentage of waterabsorbent |

TABLE 4-continued

|  | absorbent | number | (g/g) | (%) |
|---|---|---|---|---|
| example 2-17 | (2-1) | (2-1) | 15.1 | 1 |
| example 2-18 | (2-2) | (2-2) | 16.0 | 5 |
| example 2-19 | (2-3) | (2-3) | 15.8 | 10 |
| example 2-20 | (2-4) | (2-4) | 15.5 | 26 |
| example 2-21 | (2-5) | (2-5) | 16.2 | 30 |
| example 2-22 | (2-6) | (2-6) | 15.4 | 2 |
| example 2-23 | (2-7) | (2-7) | 15.1 | 19 |
| example 2-24 | (2-8) | (2-8) | 15.2 | 1 |

(part 2/2)

|  | comparative water absorbent matter | | | |
|---|---|---|---|---|
|  | No. of comparative water absorbent | number | absorption amount under pressure (g/g) | falling-off percentage of water absorbent (%) |
| comparative example 2-15 | (2-2) | (2-1) | 16.1 | 92 |
| comparative example 2-16 | (2-3) | (2-2) | 15.0 | 93 |
| comparative example 2-17 | (2-4) | (2-3) | 15.0 | 82 |
| comparative example 2-18 | (2-5) | (2-4) | 15.0 | 100 |

As seen in Table 4, a water absorbent matter, in which a water absorbent obtained from the production method of the present invention was used, is superior in the absorption amount under pressure and is very improved in the falling-off percentage of the water absorbent. The comparative water absorbent matter (2-1) showed a high falling-off percentage, because a water absorbent which was only surface-crosslinked by a crosslinking agent was used. The comparative water absorbent matter (2-2) showed a high falling-off percentage, because a water absorbent made by using ethylenediamine instead of the cationic high-molecular compound was used. The comparative water absorbent matter (2-3) showed a high falling-off percentage, because a water absorbent made by using polyethyleneimine of a low molecular weight such as a weight-average molecular weight of 2,000 or less instead of the cationic high-molecular compound was used. The comparative water absorbent matter (2 -4) showed a high falling-off percentage, because a water absorbent made by using a nonionic high-molecular compound instead of the cationic high-molecular compound was used.

Production Example 3-1

Example for Synthesizing Water-Absorbent Crosslinked Polymer (3-a)

A polymerization reaction of 4,000 parts of a 39% aqueous solution of an acrylate-based monomer, composed of 74.98 mole % of sodium acrylate, 25 mole % of acrylic acid, 0.02 mole % of trimethylolpropane triacrylate, with parts of ammonium persulfate and 0.05 parts of 1-ascorbic acid was carried out at a temperature in a range of from 30 to 80° C. under a nitrogen atmosphere, whereby a gel type water-containing crosslinked polymer was obtained. The polymer obtained is dried by a hot wind drier of 150° C., crushed by a hammer mill, and sieved by a 20 mesh metal net screen, whereby a product which passed through the 20 mash was obtained. This is called as the water-absorbent crosslinked polymer (3-a).

Example 3-1

To 100 parts by weight of the water-absorbent crosslinked polymer (3-a) were added with mixing 9 parts by weight of a 12 weight % aqueous solution of a polyamidopolyamine epichlorohydrine resin ("Kaimen 557H", made by DIG Hercules Co.), whereby the water absorbent (3-1) of present invention was obtained.

Example 3-2

To 100 parts by weight of the water-absorbent crosslinked polymer (3-a) were added with mixing 6 parts by weight of a 15 weight % aqueous solution of a polyamidopolyamine epichlorohydrine resin ("EPI-NOX P130", made by DIC Hercules Co.), whereby the water absorbent (3-2) of present invention was obtained.

Example 3-3

To 100 parts by weight of the water-absorbent crosslinked polymer (3-a) were added with mixing 7 parts by weight of a 15 weight % aqueous solution of a polyamidopolyamine epichlorohydrine resin ("SUMIREZ REZIN 650", made by Sumitomo Chemical Co., Ltd.), whereby the water absorbent (3-3) of present invention was obtained.

Example 3-4

To 100 parts by weight of the water-absorbent crosslinked polymer (3-a) were added with mixing 22 parts by weight of a 30 weight % aqueous solution of a polyamidopolyamine epichlorohydrine resin ("EPI-NOX P130", made by DIC Hercules Co., Ltd.), and a mixture obtained was heated at 120 ° C. for 5 minutes to obtain the water absorbent (3-4) of present invention.

Example 3-5

To a mixture consisting of 100 parts by weight of the water-absorbent crosslinked polymer (3-b) [a product led from "AQUALIC ® CA" (made by Nippon Shokubai Co., Ltd.) by passing it through a 50 mesh screen] and 10 parts by weight of a cellulose powder ("CF-11", made by Whatman Co., Ltd.) were added with mixing 20 parts by weight of a 30 weight % of a polyamidopolyamine epichlorohydrine resin, whereby the water absorbent (3-5) of present invention was obtained.

Example 3-6

To 100 parts by weight of the water-absorbent crosslinked polymer (3-c) ("SANWET IM-1000", made by Sanyo Chemical Industries, Ltd.) were added with mixing 16 parts by weight of a 30 weight % aqueous solution of a polyamidopolyamine epichlorohydrine resin ("SUMIREZ REZIN 650", made by Sumitomo Chemical Co., Ltd.), whereby the water absorbent (3-6) of present invention was obtained.

Comparative Example 3-1

To 100 parts by weight of the water-absorbent crosslinked polymer (3-a) were added with mixing 8 parts by weight of a 10 weight % aqueous solution of ethylene glycol glycidyl ether ("Denacol EX 810", made by Nagase Chemicals Co., Ltd.) and the mixture obtained was treated with heating at 120° C. for 10 minutes, whereby the comparative water absorbent (3-1) was obtained.

Comparative Example 3-2

To 100 parts by weight of the water-absorbent crosslinked polymer (3-a) were added with mixing a mixture solution composed of 10 parts by weight of water and 2 parts by weight of an epichlorohydrine-ethylenediamine reaction solution (a product obtained by mixing with stirring 3 parts by weight of epichlorohydrine, 0.49 parts by weight of ethylenediamine, and 30 parts by weight of methanol followed by standing them at 50° C. for 15 hours for reaction), whereby the comparative water absorbent (3-2) was obtained.

Example 3-7

Comparison of Water Absorbents

Water-absorbent properties of the water absorbents (3-1) to (3-6) of present invention, comparative water absorbents (3-1) and (3-2), and a comparative water absorbent (3-3) [water-absorbent crosslinked polymer (3-a)] themselves were compared by the forementioned methods. Results obtained are shown in Table 5.

TABLE 5

| | water absorbency (g/g) | suction power (g/g) |
|---|---|---|
| water absorbent of the present invention (3-1) | 53 | 15.3 |
| water absorbent of the present invention (3-2) | 54 | 14.6 |
| water absorbent of the present invention (3-3) | 52 | 14.3 |
| water absorbent of the present invention (3-4) | 47 | 15.8 |
| water absorbent of the present invention (3-5) | 39 | 15.2 |
| water absorbent of the present invention (3-6) | 58 | 15.3 |
| comparative water absorbent (3-1) | 44 | 16.0 |
| comparative water absorbent (3-2) | 53 | 12.3 |
| comparative water absorbent (3-3) | 57 | 12.3 |

Example 3-8

Preparation of Water Absorbent Matters

One hundred parts of the water absorbent (3-1) of present invention and 100 parts of ground pulp were mixed under a dry condition in a mixer and then, the produced mixture was pneumatically molded on a wire screen using a batch type pneumatically molding device, whereby a web having a size of 10 cm × 20 cm was obtained. The upper and lower faces of the obtained web were held between tissue papers having a basis weight of 0.0013 g/cm$^2$ and pressed with heating for 1 minute at 150° C. under a pressure of 2 kg/cm$^2$, whereby the water absorbent matter (3-1) of present invention having a basis weight of about 0.05 g/cm$^2$ was obtained. By the same procedure using the water absorbents (3-2) to (3-6) of present invention and the comparative water absorbents (3-1) to (3-3), water absorbent matters (3-2) to (3-6) of present invention and comparative water absorbent matters (3-1) to (3-3) were obtained.

Example 3-9

Evaluation of Water Absorbent Matters

The water absorbent matter (3-1) to (3-6) obtained of present invention and the comparative water absorbent matters (3-1) to (3-3) obtained were tested by the above-mentioned methods to evaluate absorption properties of the water absorbent matters. Results obtained were shown in Table 6.

TABLE 6

| | absorption amount under pressure (g/g) | falling-off percentage of water absorbent (%) |
|---|---|---|
| water absorbent matter of the present invention (3-1) | 16.3 | 33 |
| water absorbent matter of the present invention (3-2) | 15.3 | 39 |
| water absorbent matter of the present invention (3-3) | 13.8 | 44 |
| water absorbent matter of the present invention (3-4) | 15.5 | 41 |
| water absorbent matter of the present invention (3-5) | 15.5 | 35 |
| water absorbent matter of the present invention (3-6) | 11.2 | 45 |
| compative water absorbent matter (3-1) | 13.5 | 88 |
| compative water absorbent matter (3-2) | 12.3 | 87 |
| compative water absorbent matter (3-3) | 9.6 | 82 |

As seen in Table 6, the water absorbent matters of this invention are superior in the absorption amount under pressure and are very improved in the falling-off percentage of the water absorbents.

What is claimed are:

1. A water absorbent matter comprising a mat or web of cellulose fibers which contains water-absorbent resin particles, and having a density of from about 0.01 to 0.50 g/cm$^3$, said cellulose fibers being treated with a cationic high-molecular compound, said water-absorbent resin particles being contained in said mat or web of such treated cellulose fibers, being composed of a crosslinked polymer, having an acidic group on the surface and being contained among said cellulose fibers, and said cationic high-molecular compound having a weight-average molecular weight of 2,000 or more, wherein falling off of said water absorbent resin particles from said mat or web of said cellulose fibers in the presence of water is decreased by said cationic high-molecular compound.

2. A water absorbent matter comprising a mat or wed of cellulose fibers which contains water-absorbent resin particles and a cationic high-molecular compound, and having a density of from about 0.01 to 0.50 g/cm$^3$, said water-absorbent resin particles being composed of a crosslinked polymer, having an acidic group on the surface, being contained among said cellulose fibers, and being crosslinked at a part of said acidic group on the surface of the particles by a crosslinking agent having two or more of a functional group capable of a covalent bond by reacting with said acidic group, and said cationic high-molecular compound having a weight-average molecular weight of 2,000 or more, wherein falling off of said water absorbent resin particles from said mat or web of said cellulose fibers in the presence of water is decreased by said cationic high-molecular compound.

3. A water absorbent matter as claimed in claim 1, wherein said matter is a mixture of said water-absorbent resin particles and said treated cellulose fibers.

4. A water absorbent matter as claimed in any one of claims 1, 2 or 3, wherein the matter comprises from 10 to 95% by weight of the water-absorbent resin particles and from 5 to 90% by weight of the cellulose fibers.

5. A water absorbent matter as claimed in any one of claims 1, 2 or 3, wherein an amount of the cationic high-molecular compound is in a range of from about 0.1 to 30 parts by weight per 100 parts by weight of the water absorbent resin particles.

6. A water absorbent matter as claimed in any one of claims 1, 2 or 3, wherein the cationic high-molecular compound contains at least one group selected from the group consisting of a primary amino group, a secondary amino group, and a tertiary amino group as well as their salts.

7. A water absorbent matter as claimed in claim 6, wherein the cationic high-molecular compound is at least one kind selected from the group consisting of polyethyleneimine, polyamidoamine, polyetheramine, polyvinylamine, polyamidopolyamine epihalohydrine, and polyallylamine.

8. A water absorbent matter as claimed in any one of claims 1, 2 or 3, wherein the cellulose fibers are wood pulp fibers.

9. A method for producing a water absorbent matter comprising:

mixing, in a gas phase, materials for a water absorbent matter which consists essentially of water-absorbent resin particles composed of crosslinked polymer and having an acidic group on the surface, cellulose fibers, and a cationic high-molecular compound having a weight-average molecular weight of 2,000 or more; and pneumatically molding the mixture thus-obtained to form a water absorbent matter comprising a mat or web of said cellulose fibers which contains said water-absorbent resin particles and said cationic high-molecular compound and having a density of from about 0.01 to 0.50 g/cm$^3$, said water-absorbent resin particles being contained among said cellulose fibers, wherein falling off of said water absorbent resin particles from said mat or web of said cellulose fibers in the presence of water is decreased by said cationic high-molecular compound.

10. A method for producing a water absorbent matter as claimed in claim 9, wherein the material comprises the cellulose fibers and the water-absorbent resin particles, said particles being treated with the cationic high-molecular compound.

11. A method for producing a water absorbent matter as claimed in claim 9, wherein the material comprises the water-absorbent resin particles and the cellulose fibers, said fibers being treated with the cationic high-molecular compound.

12. A method for producing a water absorbent matter as claimed in any one of claims 9 to 11, wherein the water absorbent resin particles are crosslinked at a part of said acidic group on the surface of the particles by a crosslinking agent having two or more of a functional group capable of a covalent bond by reacting with said acidic group.

13. A method for producing a water absorbent matter as claimed in any one of claims 9 to 11, comprising, after pneumatically molding the mixture, putting the molded product between tissue papers and pressing this to become one body.

14. A method for producing a water absorbent matter as claimed in claim 13, wherein heating is carried out when the pressure is applied.

15. A method for producing a water absorbent comprising, treating the surface of water-absorbent resin particles, which comprise a crosslinked polymer and have an acidic group on the surface, with a crosslinking agent having two or more of a functional group capable of a covalent bond by reacting with said acidic group in order to carry out crosslinking by a part of said acidic group, then mixing the particles with a cationic high-molecular compound having a weight-average molecular weight of 2000 or more, which is capable of making an ionic bond through reaction with the acidic group.

16. A method for producing a water absorbent as claimed in claim 15, wherein said crosslinking agent comprises a compound having two or more of the functional group of at least one kind selected from he group consisting of an epoxy group, and aldehyde group, and a hydroxyl group.

17. A method for producing a water absorbent as claimed in claim 16, wherein a said crosslinking agent is selected from the group consisting of a polyglycidyl ether, a haloepoxy compound, a polyaldehyde, and a polyol.

18. A method for producing a water absorbent as claimed in any one of claims 15 to 17, wherein the cationic high-molecular compound contains at least one group selected from the group consisting of a primary amino group, a secondary amino group, and a tertiary amino group as well as their salts.

19. A method for producing a water absorbent as claimed in claim 18, wherein the cationic high-molecular compound is selected from the group consisting of polyethyleneimine, polyamidoamine, polyetheramine, polyvinylamine, polyamidopolyamine epihalohydrine, and polyallylamine.

20. A method for producing a water absorbent as claimed in any one of claims 15 to 17, wherein the water-absorbent resin particles treated with said crosslinking agent are mixed with said cationic high molecular compound in the presence of water to make the cationic high molecular compound react with an acidic group remaining on the surface of said particles.

21. A method for producing a water absorbent as claimed in claim 20, wherein drying is carried out after reaction of the cationic high molecular compound with the acidic group.

22. A water absorbent comprising a water-absorbent crosslinked polymer and a polyamidopolyamine epihalohydrine resin.

23. A water absorbent as claimed in claim 22, wherein the water-absorbent crosslinked polymer is an acrylate crosslinked polymer.

24. An absorbent matter comprising a mat or web of cellulose fibers which contains the water absorbent as claimed in claim 22 and having a density of from about 0.01 to 0.50 g/cm³, said particles of the water absorbent crosslinked polymer being contained among said cellulose fibers.

25. An absorbent matter as claimed in claim 24, wherein the cellulose fibers are wood pulp fibers.

26. A method for producing an absorbent matter characterized by mixing the water absorbent as claimed in claim 22 with cellulose fibers in a dry condition, and then compressing an obtained mixture to form said absorbent matter comprising a matter web of said cellulose which contains said water absorbent and having a density of from about 0.01 to 0.50 g/cm³, said particles of the water absorbent crosslinked polymer being contained among said cellulose fibers.

27. A method for producing an absorbent matter as claimed in claim 26, wherein the compressing is carried out under heating.

28. A method for producing a water absorbent comprising mixing a polyamidopolyamine epihalohydrine resin with a water-absorbent crosslinked polymer.

29. A method for producing a water absorbent as claimed in claim 28, wherein the mixing is carried out in the presence of water.

* * * * *